United States Patent
Minamitani et al.

(10) Patent No.: US 8,104,355 B2
(45) Date of Patent: Jan. 31, 2012

(54) THERMAL HUMIDITY SENSOR

(75) Inventors: Rintaro Minamitani, Tsukuba (JP); Keiji Hanzawa, Mito (JP); Akio Yasukawa, Kashiwa (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 144 days.

(21) Appl. No.: 12/707,438

(22) Filed: Feb. 17, 2010

(65) Prior Publication Data

US 2010/0218614 A1    Sep. 2, 2010

(30) Foreign Application Priority Data

Feb. 27, 2009 (JP) ................................. 2009-045039

(51) Int. Cl.
*G01L 9/02* (2006.01)

(52) U.S. Cl. .................. 73/725; 73/719; 73/734; 73/754

(58) Field of Classification Search ........................ None
See application file for complete search history.

(56) References Cited

U.S. PATENT DOCUMENTS

| | | | |
|---|---|---|---|
| 5,291,781 A | | 3/1994 | Nagata et al. |
| 5,804,720 A | * | 9/1998 | Morimasa et al. ......... 73/204.26 |
| 6,450,025 B1 | * | 9/2002 | Wado et al. ................. 73/204.26 |
| 2002/0189375 A1 | * | 12/2002 | Takeuchi et al. ................. 73/865 |
| 2010/0077851 A1 | * | 4/2010 | Minamitani et al. ....... 73/204.26 |

FOREIGN PATENT DOCUMENTS

| | | |
|---|---|---|
| EP | 1 291 621 A1 | 3/2003 |
| EP | 1 936 364 A1 | 6/2008 |
| JP | 4-230808 A | 8/1992 |
| JP | 2000-111377 A | 4/2000 |
| JP | 2001-50787 A | 2/2001 |
| JP | 2005-308676 A | 11/2005 |

OTHER PUBLICATIONS

Japanese Office Action Dated May 10, 2011 (three(3) pages).
European Search Report dated Jul. 19, 2010 (Three (3) pages).

* cited by examiner

*Primary Examiner* — Andre Allen
(74) *Attorney, Agent, or Firm* — Crowell & Moring LLP (57) ABSTRACT

A measurement element includes a semiconductor substrate with electrical insulating film formed thereon. A resistor formed on the electrical insulating film constitutes a heater; and a cavity is formed by removing a portion of the semiconductor substrate that corresponds to a region where a body part of the resistor is formed. The region where the body part of the resistor is formed is formed into a thin wall part by the cavity, and an opening and a slit is formed in a portion of the thin wall part in such a manner as to penetrate the thin wall part in the thickness direction. The measurement element has a film formed covering the region of the opening or slit.

7 Claims, 6 Drawing Sheets

THERMAL HUMIDITY SENSOR

TECHNICAL FIELD

The present invention relates to a measurement element having a thin wall part or a thin film part, such as a diaphragm part, a bridge part, or a cantilever structure part, for thermally insulating a resistor constituting a heater, from a semiconductor substrate.

BACKGROUND ART

A measurement element including a resistor which constitutes a heater and is thermally insulated from a semiconductor substrate is conventionally known. Such measurement element is formed using a semiconductor thin film formation technique and a micromachining technique.

A diaphragm sensor formed as follows is an example of such measurement element (see Patent Literature 1). Specifically, through anisotropic etching, an opening is formed in a semiconductor substrate at a central part on the back side thereof. The opening has a trapezoidal cross section and does not penetrate the top surface of the semiconductor substrate. Then, a thin-wall diaphragm part is formed on a bottom side of the opening, namely, on a top surface side of the semiconductor substrate. Using the thin film formation technique, a thin-film heater element and a thin-film resistance thermometer element are formed on a central portion of the top surface of the diaphragm part. In this diaphragm sensor, the formation of the diaphragm part allows the diaphragm part to be thermally insulated from the semiconductor substrate. Moreover, in the diaphragm part between the heater element and the resistance thermometer element, a slit part penetrating the diaphragm part is provided. Thereby, thermal conduction from the heater element to the resistance thermometer element is reduced. Multiple slit parts penetrating the diaphragm part are further provided in the diaphragm part between the heater element and a diaphragm periphery part, namely a thick wall part of the semiconductor substrate, and between the resistance thermometer element and the diaphragm periphery part. Thereby, thermal conduction from the heater element and the resistance thermometer elements to the thick wall part of the semiconductor substrate is reduced.

An another example of the measurement element is a heater device (see Patent Literature 2) including a silicon substrate in which a cavity part is formed, a thin film thermally isolated from the silicon substrate by the cavity part, a thermo-sensitive resistor having a thin-film heater and a thin-film temperature sensor formed on the thin film. In this heater device, the cavity part is formed by etching removal of the silicon substrate from a side of the silicon substrate where the thin-film heater and the thin-film temperature sensor are formed, to such a degree that the cavity part does not penetrate the back side of the silicon substrate. The thin film on which the thin-film heater and the thin-film temperature sensor are formed constitutes a bridge part bridging across the cavity part. In such a structure, the cavity part has an opening in the thin film around the bridge part. Patent Literature 2 discloses that a cantilever structure may be employed instead of the bridge part. When the cantilever structure is employed, the cavity part has an opening in the thin film around the cantilever structure part.

CITATION LIST

Patent Literatures

[Patent Literature 1] Japanese Patent Application Publication No. H04-230808
[Patent Literature 2] Japanese Patent Application Publication No. 2005-308676

SUMMARY OF INVENTION

Technical Problems

A thin wall part or a thin film part, such as a diaphragm part, a bridge part, or a cantilever structure part is usually formed of an electrical insulating film for the purpose of thermally insulating a resistor constituting a heater, from a semiconductor substrate. The electrical insulating film is often made of an inorganic, brittle material, such as, for example, silicon dioxide ($SiO_2$) or silicon nitride ($Si_xN_y$). When a film made of a brittle material has a crack, a delayed defect sometimes occurs in which the film breaks without any prior warning. Since the thin wall part or the thin film part is very thin, a slight defect may lead to a breakage no matter what the material is. Accordingly, a sensor having a diaphragm which will not satisfy an assumed life period due to a defect in a manufacturing process needs to be removed completely. A process for removing a sensor having a damaged diaphragm not satisfying the assumed life period is called screening.

Further, in a dicing process in the manufacture of the measurement element, if a solid particle, such as a cutoff of semiconductor substrate included in cooled water, collides against the electrical insulating film constituting the thin wall part or the thin film part, such as a diaphragm part, a bridge part, or a cantilever structure part, the thin wall part or the thin film part may break. Thus, the electrical insulating film constituting the thin wall part or the thin film part needs to be prevented from breaking in the dicing process in the manufacture. The dicing process is normally performed after the screening process. For this reason, if the dicing process is performed after the screening process, the electrical insulating film constituting the thin wall part or the thin film part needs to be prevented from breaking after the screening process.

An object of the present invention is to provide a structure unlikely to break in the dicing process while allowing easy execution of screening, for a measurement element in which a resistor constituting a heater is formed on a thin wall part thermally insulated from a semiconductor substrate by providing a cavity part formed in the semiconductor substrate.

Solution to Problems

In order to achieve the above object, a measurement element of the present invention includes a semiconductor substrate; an electrical insulating film formed on the semiconductor substrate; a resistor formed on the electrical insulating film, the resistor constituting a heater; and a cavity part formed by removing a portion of the semiconductor substrate that corresponds to a region where a body part of the resistor is formed, wherein the region where the body part of the resistor is formed is formed into a thin wall part by the cavity part, any of an opening and a slit is formed in a portion of the thin wall part in such a manner as to penetrate the thin wall part in a thickness direction thereof, and a film is formed covering a region of the opening or the slit.

In this regard, the electrical insulating film is preferably formed on a top surface of the semiconductor substrate, and the cavity part is formed from a back surface toward the top surface of the semiconductor substrate.

The film covering the region of the opening or the slit is preferably an organic film.

The organic film is preferably a resin having heat resistance such as polyimide.

The film covering the region of the opening or the slit may be formed as an electric insulating film thinner than the electrical insulating film constituting the thin wall part on which the body part of the resistor is formed.

A rim of the opening or the slit is preferably located inward of a rim of the cavity part.

In order to achieve the above object, a measurement element of the present invention preferably includes: a semiconductor substrate; an electrical insulating film formed on the semiconductor substrate; a resistor formed on the electrical insulating film, the resistor constituting a heater; and a cavity part formed by removing a portion of the semiconductor substrate that corresponds to a region where a body part of the resistor is formed, wherein the region where the body part of the resistor is formed is formed into a thin wall part by the cavity part, any of an opening and a slit is formed in a portion of the thin wall part in such a manner as to penetrate the thin wall part in a thickness direction thereof, and wherein the electrical insulating film is formed on a top surface of the semiconductor substrate; the cavity part is formed from a back side toward a top side, of the semiconductor substrate; the film covering the region of the opening or the slit is formed before the opening or the slit is formed; and the opening or the slit is formed from a side where the cavity part is formed.

Advantageous Effects of Invention

According to the present invention, the structure covering the opening or the slit with the film allows to perform a screening test, which involves pressurizing, at wafer level, the thin wall part formed on the region where the body part of the resistor is formed. Thereby, a measurement element having a manufacture defect can be removed. In addition, according to the present invention, the film covering a region of the opening or the slit allows to reinforce particularly the support structure of the thin wall part formed on the region where the body part of the resistor is formed. This can prevent the thin wall part from breaking due to dust collision occurring in the dicing process.

DESCRIPTION OF EMBODIMENTS

Embodiments according to the present invention will be described below.

Embodiment 1

Figure 1A:
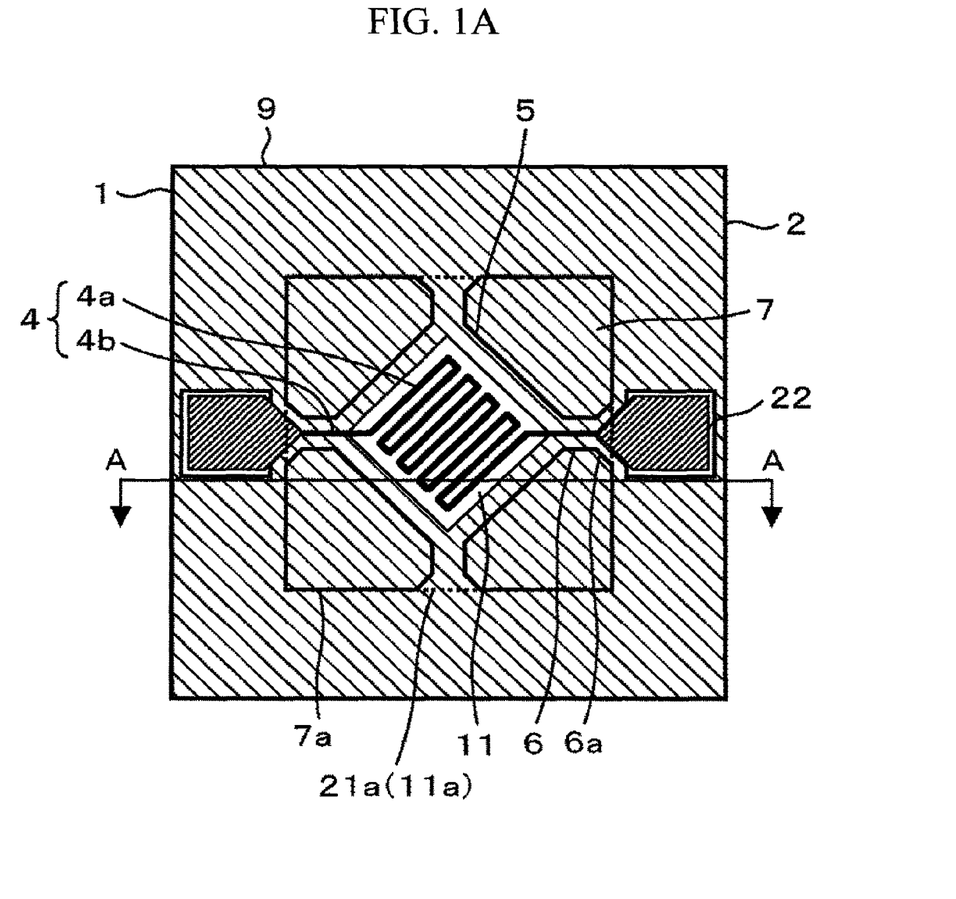
FIG. 1A is a schematic plan view of an embodiment of a measurement element provided to a thermal humidity sensor to which the present invention is applied.
Figure 1B:
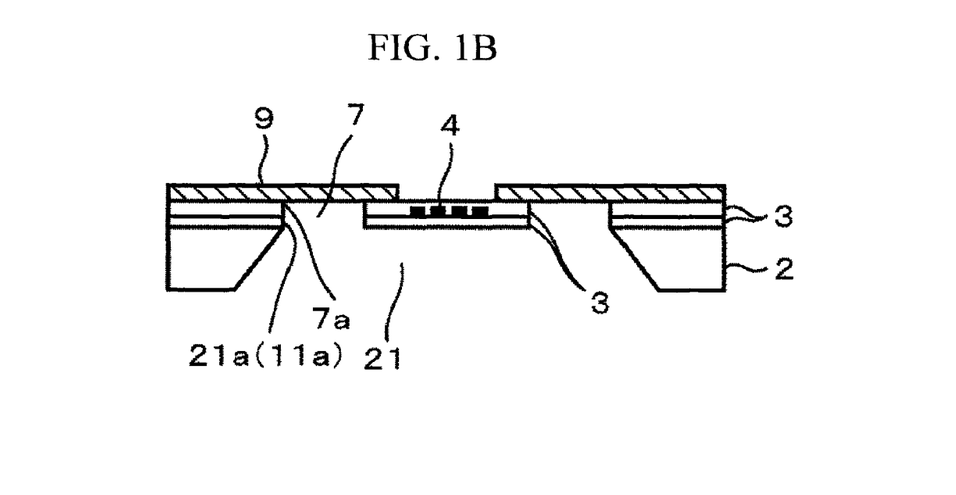
FIG. 1B is an enlarged cross-sectional view, taken along the A-A line in FIG. 1A.
Figure 2A:
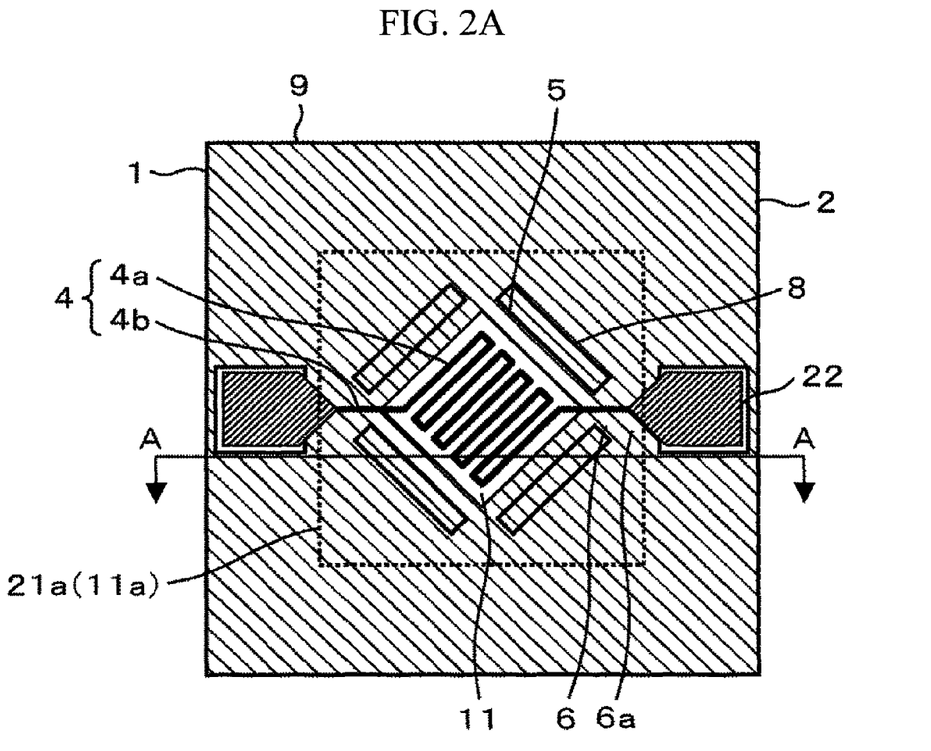
FIG. 2A is a schematic plan view of an embodiment of a measurement element provided to a thermal humidity sensor to which the present invention is applied.
Figure 2B:
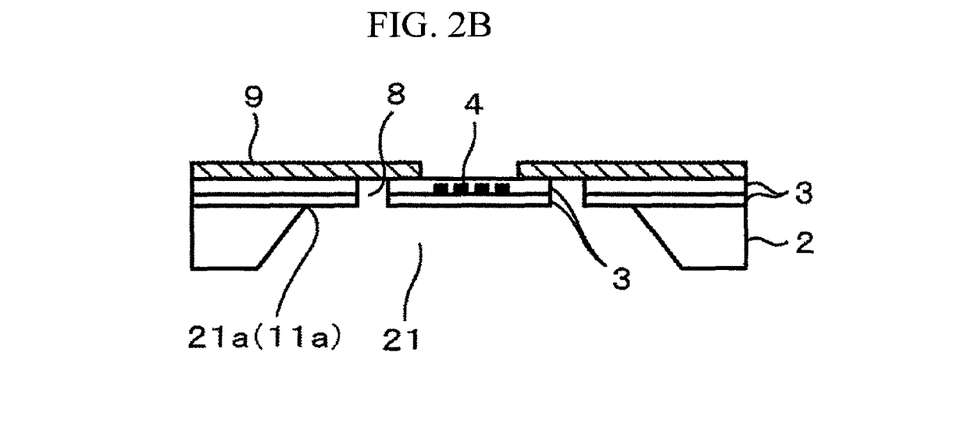
FIG. 2B is an enlarged cross-sectional view, taken along the A-A line in FIG. 2A.

As an example, a thermal humidity sensor to which a diaphragm sensor of the present invention is applied is described below. FIGS. 1A and 2A are schematic plan views of a measurement element 1 of the humidity sensor. FIGS. 1B and 2B are enlarged cross-sectional views, taken along the A-A line in FIGS. 1A and 2A, respectively. As shown in FIGS. 1 and 2, the measurement element 1 provided to the thermal humidity sensor of the present embodiment includes a semiconductor substrate 2, an electrical insulating film 3, a resistor 4, and others. The resistor 4 may be formed by folding back multiple times. In the meantime, the structure of the resistor is different depending on the measurement method, and one example of possible structures is shown here.

The semiconductor substrate 2 is made of single-crystal silicon or the like, and the electrical insulating film 3 is formed on the top surface of the semiconductor substrate 2. The electrical insulating film 3 is a film having electrical insulating properties and thermal insulating properties, such as, for example, a silicon dioxide ($SiO_2$) film or a silicon dioxide ($SiO_2$) film reinforced with a silicon nitride ($Si_xN_y$) film. The resistor 4 and the like are formed on the electrical insulating film 3. The resistor 4 is made of a semiconductor material such as, for example, polycrystal silicon, germanium, gallium arsenide, tantalum, molybdenum, or platinum. A portion of the semiconductor substrate 2 that corresponds to a region where the resistor 4 is formed on the electrical insulating film 3 is removed through anisotropic etching in a thickness direction of the semiconductor substrate 2 from the back side of the semiconductor substrate 2 to an interface surface between the semiconductor substrate 2 and the electrical insulating film 3, thus forming a cavity 21 in the semiconductor substrate 2. In the present embodiment, the resistor 4 constitutes a heating resistor, namely, a heater. Accordingly, the cavity 21 insulates the resistor 4 thermally. In the meantime, the cavity 21 is also called a cavity part.

The resistor 4 includes a body part 4a and lead parts 4b. An end portion of each of the lead parts 4b is electrically connected to a corresponding terminal electrode 22 formed on an edge part of the measurement element 1. The terminal electrodes 22 and the lead parts 4b are each formed by plating or vapor deposition of a conductive material, such as gold or aluminum. Strictly, the resistor 4 means the body part 4a in the following descriptions.

In the thermal humidity sensor, application of a voltage to the resistor 4 causes the resistor 4 to heat itself. When the amount of moisture in the atmosphere increases, more heat is conducted by the moisture. Consequently, the heat of the resistor 4 is dissipated more. Utilizing this temperature decrease in the resistor 4 along with an increase in the amount of moisture, the absolute humidity in the atmosphere can be measured. It is preferable to set the temperature of the resistor 4 to 300° C. or higher, which causes a great change in the thermal conduction by moisture. While many measurement methods have been proposed for the thermal humidity sensor, every method utilizes the fact that the thermal conductivity of moisture is different depending on the amount of the moisture. Accordingly, thermal conduction from the heated resistor 4 to the semiconductor substrate 2 through the electrical insulating film 3 and support parts 6 leads to a measurement error in the absolute humidity. To minimize the thermal conduction to the semiconductor substrate 2, a sensor part 5 needs to be thermally insulated.

The reason for providing a diaphragm 11 is to thermally insulate the resistor 4 from the semiconductor substrate 2. Further improvement in the thermal insulation of the sensor part 5 is achieved by forming openings 7 (see FIG. 1) or slits 8 (see FIG. 2) in the peripheral area of the sensor part 5 of the diaphragm 11. The openings 7 or the slits 8 penetrate the diaphragm 11 in the through-thickness direction of the diaphragm 11.

An organic protection film 9, which is a soft, electrically-insulating film, is formed covering the openings 7 or the slits 8. In other words, the organic protection film 9 is formed covering a part other than the parts where the resistor 4 and the terminal electrodes 22 are respectively formed. Since the resistor 4 is kept at 300° C. or higher during operation, it is preferable not to form the organic protection film 9 on the sensor part 5 to prevent deterioration of the organic protection film 9. Further, to allow electric connection, the organic protection film 9 is not formed on an edge part of the electrical insulating film 3 where each of the terminal electrodes 22 of the measurement element 1 is formed.

In the present embodiment, the openings 7 and the slits 8 each penetrate the diaphragm 11 in the through-direction of the diaphragm 11. Hence, the concept of the slits 8 is included in the concept of the openings 7.

In a case where the humidity sensor is used for an internal combustion engine of an automobile or the like, since the engine sucks outside air, the air to be a target for flow measurement includes solid particles such as sand, salt, and dust. To remove such particles in sucked outside air, the internal combustion engine of an automobile or the like, for example, is normally provided with an air filter having a mesh size of 15 μm. Although a particle having a diameter larger than about 15 μm is removed by the air filter, a particle having a diameter equal to or smaller than about 15 μm passes through the air filter. In a humidity sensor, air flow causes a measurement error, and therefore a windshield structure is provided to stop air flow. In some windshield structures, a solid particle sometimes collides directly against the measurement element 1. Accordingly, with only the electrical insulating film 3 made of silicon dioxide being a brittle, inorganic material, the support parts 6 cannot deform enough to absorb a kinetic energy generated in collision of the particle, causing a local stress at the position of the collision. Consequently, the support parts 6, where a maximum stress is received, may break. In other words, the support parts 6 break when the kinetic energy of the particle is larger than the deformation energy of the electrical insulating film 3 (the absorption energy of the electrical insulating film 3).

Even if the windshield structure can prevent the support parts 6 from being broken by a solid particle flowing in during operation, the support parts 6 still may break in a dicing process in the manufacture. This is because a solid particle included in cooled water used in the dicing process may collide against the support parts 6 as a solid particle included in atmosphere during operation does.

The organic protection film 9 made of an organic material such as polyimide has a more energy absorption capability than the electrical insulating film 3 such as a silicon-dioxide (SiO2) film. For this reason, when a particle collides in the measurement element 1 including the organic protection film 9 made of polyimide or the like, not only do the support parts 6 being a weakest part deform, but also the organic protection film 9 itself absorbs the collision energy of the particle. Consequently, it can be prevented that the particle collision or its backfire pressure breaks the support parts 6, and accordingly breaks the measurement element 1.

In the meantime, the organic protection film 9 is formed covering a part other than the parts where the heating resistor 4 and the terminal electrode 22 are respectively formed. In other words, the organic protection film 9 is formed covering the openings or the slits. The protection film near the heating resistor is exposed to a high temperature of 300° C. or higher.

Thus, a film made of polyimide is suitable for the protection film because polyimide is an organic material excellent in heat resistance. However, a different organic material may be used if, for example, the measurement device 1 is used for measurement under a constant temperature of 300° C. or lower.

Figure 6:
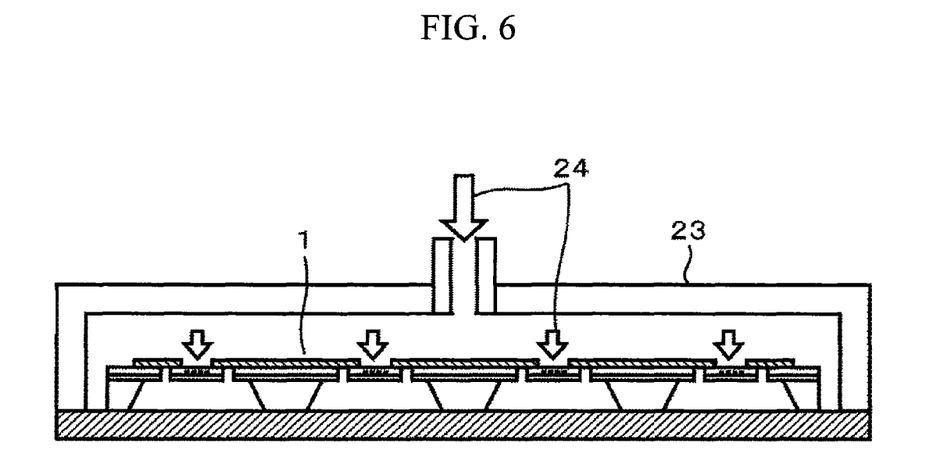
FIG. 6 is a schematic view of a pressure screening device.

As described above, the electrical insulating film 3 of the diaphragm sensor is made of an inorganic, brittle material or the like. If the electrical insulating film 3 made of such material has a slight defect (crack), the electrical insulating film 3, accordingly the diaphragm 11, breaks without any prior warning (delayed defect) due to load during operation, making the measurement impossible. Accordingly, a screening test needs to be conducted to remove a diaphragm having a manufacture defect. In the screening test, a load corresponding to that in an actual operational environment is applied, and a diaphragm having a crack that led to breakage within an assumed life period is removed. A method of applying the load includes mechanical load application and thermal load application. The mechanical load application requires a shorter test time and therefore is appropriate for the structure employed here, because the object is to remove a diaphragm having the sensor support parts 6 in which a crack has been caused at an early stage. A method of the mechanical load application includes pressure screening and probe-insertion screening. As FIG. 6 shows, the pressure screening can evenly apply, in a pressure chamber 23, a pressure 24 to an entire surface of a wafer on which multiple measurement elements 1 are formed, and therefore can achieve highly-accurate screening with a short time. Since several hundred measurement elements 1 are formed on a single wafer, the probe-insertion screening requires a long time. Moreover, it is difficult to perform accurate measurement with the probe-insertion screening because the length of probe insertion is in the microns scale.

To perform the pressure screening, the sensor needs to be shielded at the upper face and the lower face which is namely the cavity 21. Accordingly, when the diaphragm has the openings 7 or the slits 8, the pressure screening cannot be conducted. On the other hand, when the diaphragm has a structure such that the openings 7 or the slits 8 are covered with the organic protection film 9, the upper side and the lower side of the diaphragm can be isolated from each other, making the pressure screening possible. Therefore, a diaphragm sensor having a crack caused in an early stage can be removed using the pressure screening when the openings 7 and the slits 8 are covered with the organic protection film 9. As a result, a highly reliable diaphragm sensor can be provided.

When the diaphragm has the openings 7 or the slits 8, there is a risk that dust enters from the openings 7 or the slits 8. If dust keeps entering and being deposited on the back of the sensor part, the deposited dust might cause a decrease in the thermal insulation performance. However, dust does not enter to be deposited on the back of the sensor part when the openings 7 and the slits 8 are covered with the organic thin film. Accordingly, with this structure, the properties are unlikely to change for a long period of time.

In addition, the organic film has a lower rigidity than the insulating film by more than a digit. For this reason, when the openings 7 are formed in the diaphragm (FIG. 1), the organic protection film 9 deforms greatly into a concave by the pressure during operation. This leads to a risk that dust stays in the concave of the organic protection film 9 and decreases the thermal insulating properties. When the slits 8 are formed in the diaphragm (FIG. 2), on the other hand, the diaphragm has thermal insulating properties equivalent to that having the openings 7, and the organic protection film 9 does not greatly deform by pressure fluctuation during operation. As a result, the thermal insulating properties are not decreased by the dust.

Summing up the present embodiment, the measurement element is configured as follows.

The measurement element has the semiconductor substrate 2, the electrical insulating film 3 formed on the semiconductor substrate 2, the resistor 4 constituting a heater and being formed on the electrical insulating film 3, and the cavity 21 (cavity part) formed by removing a portion of the semiconductor substrate 2 that corresponds to a region where the body part 4a of the resistor 4 is formed. The region where the body part 4a of the resistor 4 is formed is formed into a thin wall part (diaphragm) by the cavity 21. The openings 7 or the slits 8 are formed in a portion of the thin wall part in such a manner as to penetrate in the thickness direction of the thin wall part. In this measurement element 1, before forming the cavity 21, the electrical insulating film 3 is formed on the top surface of the semiconductor substrate 2, and the organic protection film 9 is formed on the electrical insulating film 3. After the formation of the electrical insulating film 3 and the organic protection film 9, the cavity 21 is formed from the back side toward the top side of the semiconductor substrate 2. Then, the openings 7 or the slits 8 are formed in the electrical insulating film 3 constituting the thin wall part, from the side where the cavity 21 is formed, while leaving the organic protection film 9.

The diaphragm 11 is employed in the present embodiment as the thin wall part or thin film part on which the resistor 4 constituting a heater is placed. However, other structures such as a bridge structure or a cantilever structure may be employed instead. Accordingly, the thin wall part or the thin film part includes the diaphragm structure, the bridge structure, and the cantilever structure.

Although the following embodiments each describe a case where the openings 7 are formed, it is of course possible to employ the slits 8 instead of the openings 7. Further, it is a matter of course that the above-described structure may be combined with any of structures of the embodiments to be described below.

Note that, in the example in FIG. 1, a portion of a rim 7a of each opening 7 overlaps with a rim 21a of the cavity 21 (i.e., with a rim 11a of the diaphragm 11).

Embodiment 2

Figure 3A:
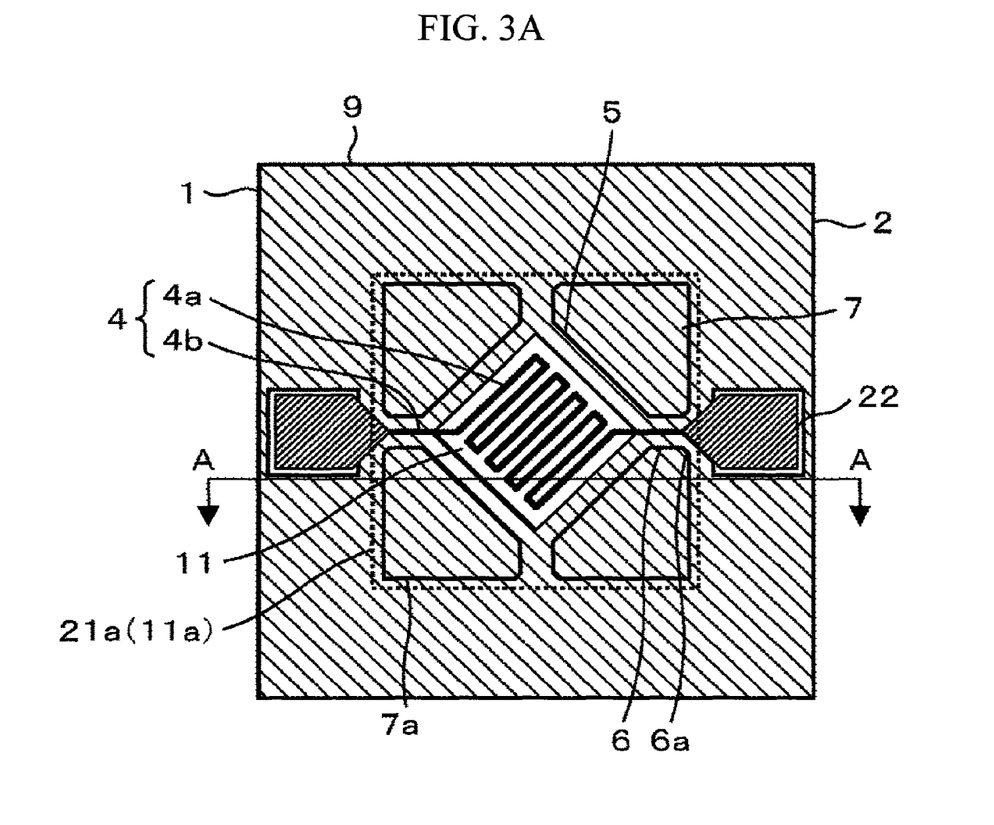
FIG. 3 shows another embodiment of a thermal humidity sensor to which the present invention is applied.
Figure 3B:
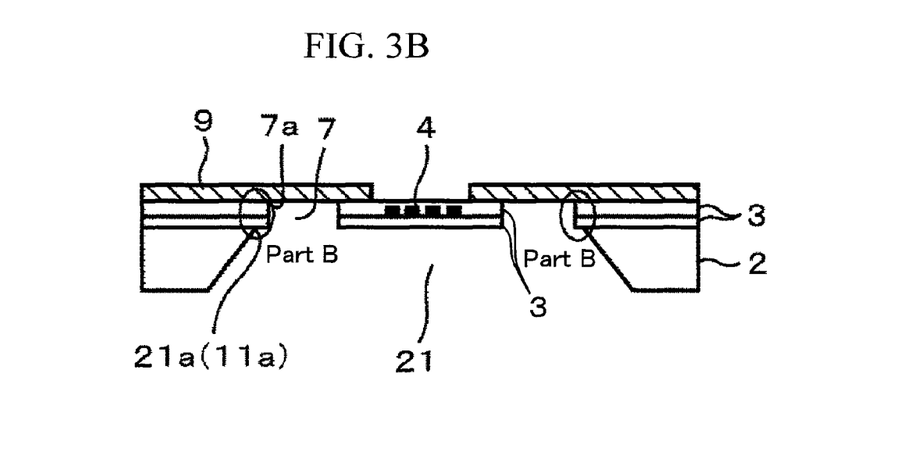

FIG. 3 shows another embodiment of the present invention. In a structure of the present embodiment, the rim 21a of the cavity 21 does not coincide with the rim 7a of the opening 7. Specifically, in this structure, a root part 6a of each support part 6 is shifted inward of the rim 21a of the cavity 21. When the rim 21a of the cavity 21 coincides with the rim 7a of the opening 7, the root part 6a of the support part 6 is restricted from deforming, and therefore is a weakest part (maximum stress part) against a concentrated load such as dust collision. In the structure in which the rim 7a of the opening 7 is shifted inward of the rim 21a, a part denoted by B in FIG. 3 deforms in response to a concentrated load. Therefore, the structure has an effect that a stress at the root part 6a of the support part 6 is reduced.

Note that, in the present embodiment, the openings 7 include slit-shaped openings.

Embodiment 3

Figure 4A:
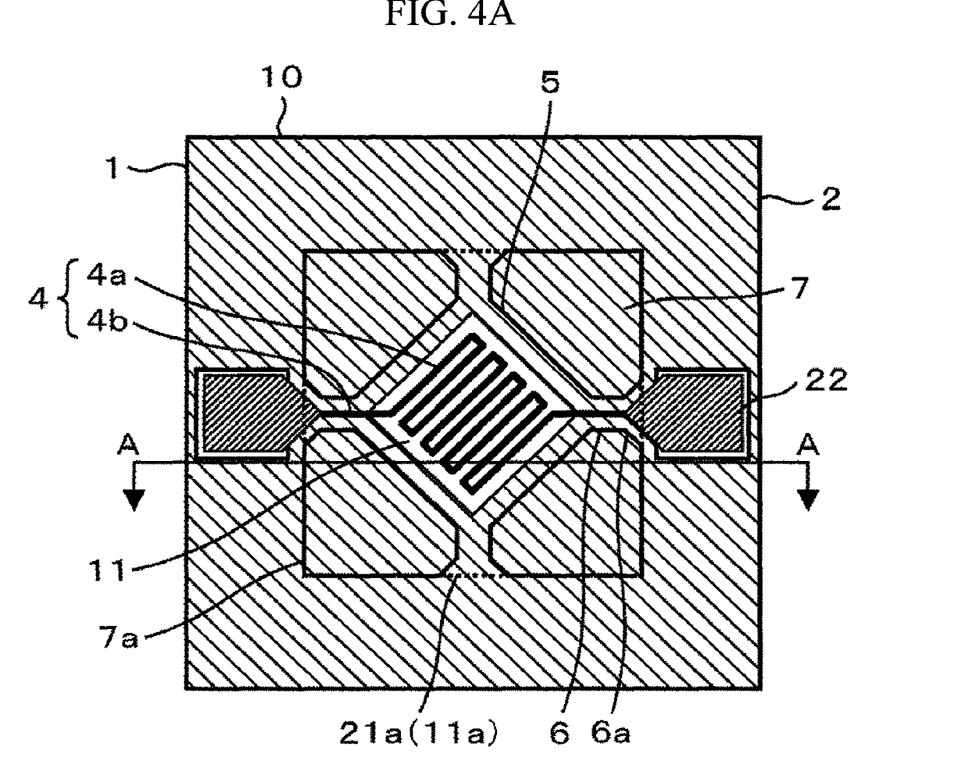
FIG. 4 shows yet another embodiment of a thermal humidity sensor to which the present invention is applied.
Figure 4B:
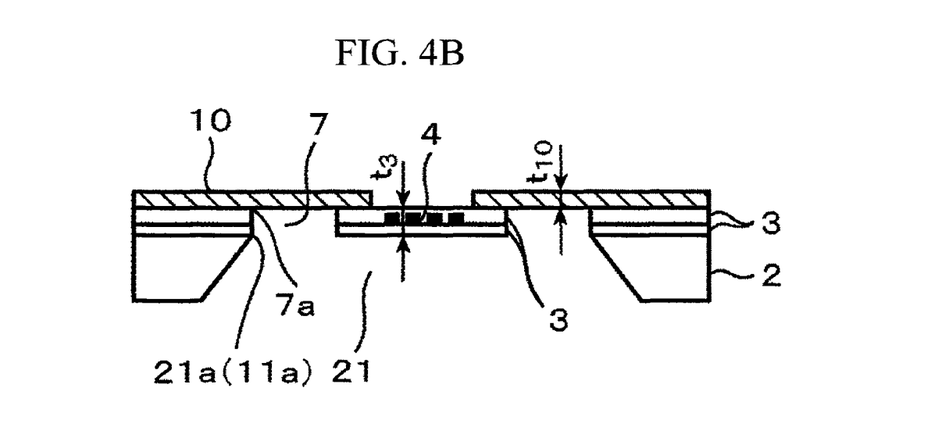

FIG. 4 shows yet another embodiment of the present invention. In the present embodiment, an inorganic protection film 10 is formed in place of the organic protection film 9. The inorganic protection film 10 is made of the same material as the electrical insulating film 3. The electrical insulating film 3 formed on the semiconductor substrate 2 is a film having electrical insulating properties and thermal insulating properties, such as, for example, a silicon dioxide ($SiO_2$) film or a silicon dioxide ($SiO_2$) film reinforced with a silicon nitride ($Si_xN_y$) film. Since the inorganic protection film 10 is made of the same material as the electrical insulating film 3 of the sensor part, a thickness $t_{10}$ of the inorganic protection film 10 is made thinner than a thickness $t_3$ of the electrical insulating film 3 to improve the thermal insulating properties. As described earlier, the electrical insulating film 3 made of an inorganic material has a risk of being broken by dust collision. However, when a structure for eliminating a measurement error caused by air flow, such as the windshield structure, is provided, there is no need to consider the dust collision. Accordingly, the structure of the present embodiment can be employed.

Embodiment 4

Figure 5A:
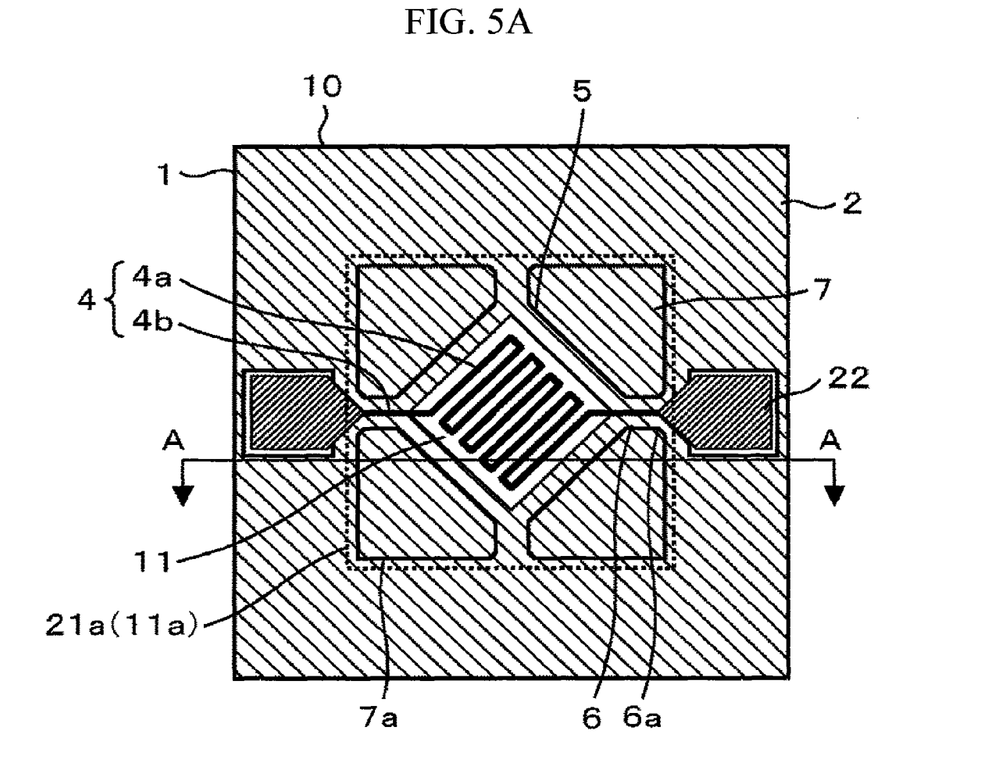
FIG. 5 shows still another embodiment of a thermal humidity sensor to which the present invention is applied.
Figure 5B:
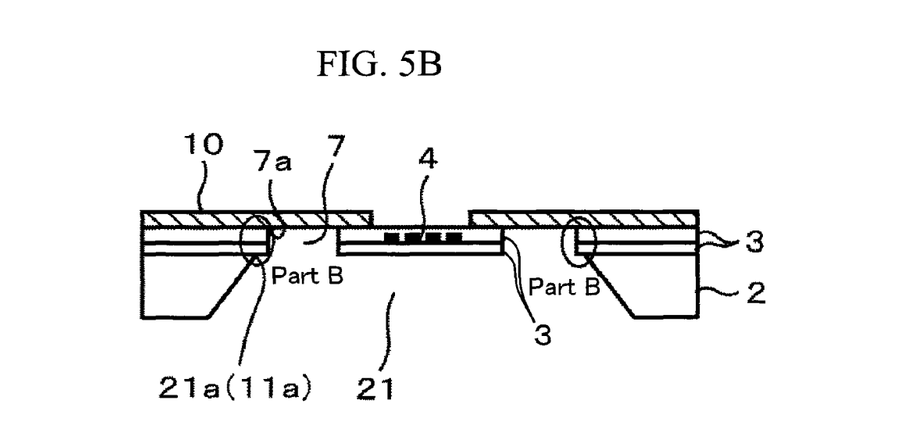

FIG. 5 shows still another embodiment of the present invention. In a structure of the present embodiment, the rim 21a of the cavity 21 does not coincide with the rim 7a of the opening 7. Specifically, in this structure, the root part 6a of each support part 6 is shifted inward of the rim 21a of the cavity 21. When the rim 21a of the cavity 21 coincides with the rim 7a of the opening 7, the root part 6a of the support part 6 is restricted from deforming, and therefore is a weakest part (maximum stress part) against a concentrated load such as dust collision. In the structure in which the opening 7 is shifted inward of the rim 21a, a part denoted by B in FIG. 5 deforms in response to a concentrated load. Therefore, the structure has an effect that a stress at the root part 6a of the support part 6 is reduced. Moreover, as FIG. 5 shows, the thickness of the electrical insulating film is large at the rim part of the edge of the diaphragm; accordingly, the value of a stress at the edge of the diaphragm can be reduced.

In the embodiments described above, only one type of the resistor 4 is described. However, besides the heating resistor constituting a heater, a resistance thermometer that measures a temperature, or the like, can be placed on the diaphragm part or around the diaphragm part. In this way, each of the above embodiments can be implemented not only for a humidity sensor, but also for other various types of measurement elements by placing a heater on a thin wall part thermally insulated from a semiconductor substrate and by placing an appropriate one of various types of a resistor and a sensitive member on the thin wall part or around the thin wall part, depending on a measurement target.

In addition, in the present embodiment, the diaphragm structure is employed as the thin wall part or the thin film part on which the heater is placed. However, a bridge structure or a cantilever structure may be employed instead. Accordingly, the thin wall part or the thin film part includes a diaphragm structure, a bridge structure, and a cantilever structure.

REFERENCE SIGNS LIST

1 measurement element
2 semiconductor substrate
3 electrical insulating film
4 resistor
5 sensor part
6 support part
6a root part of the support part 7 opening
8 slit
9 organic protection film
10 inorganic protection film
21 cavity
22 terminal electrode
23 pressure chamber
24 pressure

The invention claimed is:

1. A measurement element comprising:
a semiconductor substrate;
an electrical insulating film formed on the semiconductor substrate;
a resistor formed on the electrical insulating film, the resistor constituting a heater; and
a cavity part formed by removing a portion of the semiconductor substrate that corresponds to a region where a body part of the resistor is formed, wherein
the region where the body part of the resistor is formed is formed into a thin wall part by the cavity part,
any of an opening and a slit is formed in a portion of the thin wall part in such a manner as to penetrate the thin wall part in a thickness direction thereof, and
a film is formed covering a region of the opening or the slit.

2. The measurement element according to claim 1, wherein
the electrical insulating film is formed on a top surface of the semiconductor substrate, and
the cavity part is formed from a back surface toward the top surface of the semiconductor substrate.

3. The measurement element according to claim 1, wherein the film covering the region of the opening or the slit is an organic film.

4. The measurement element according to claim 3, wherein the organic film is made of polyimide.

5. The measurement element according to claim 1, wherein the film covering the region of the opening or the slit is formed as an electric insulating film thinner than the electrical insulating film constituting the thin wall part on which the body part of the resistor is formed.

6. The measurement element according to claim 1, wherein a rim of the opening or the slit is located inward of a rim of the cavity part.

7. A measurement element comprising:
a semiconductor substrate;
an electrical insulating film formed on the semiconductor substrate;
a resistor formed on the electrical insulating film, the resistor constituting a heater; and
a cavity part formed by removing a portion of the semiconductor substrate that corresponds to a region where a body part of the resistor is formed, wherein
the region where the body part of the resistor is formed is formed into a thin wall part by the cavity part,
any of an opening and a slit is formed in a portion of the thin wall part in such a manner as to penetrate the thin wall part in a thickness direction thereof,
before forming the cavity part, the electrical insulating film is formed on a top surface of the semiconductor substrate, and an organic film is formed on the electrical insulating film,
after forming the electrical insulating film and the organic film, the cavity part is formed from a back surface toward the top surface of the semiconductor substrate, and
the opening or the slit is formed in the electrical insulating film constituting the thin wall part, from a side where the cavity part is formed, while leaving the organic film unremoved.

* * * * *